US008540975B2

(12) United States Patent
Verboom et al.

(10) Patent No.: US 8,540,975 B2
(45) Date of Patent: Sep. 24, 2013

(54) HAIR STYLING METHOD

(75) Inventors: Gilles M Verboom, St. Charles, IL (US); Jean Louise Razon Navarro, Chicago, IL (US)

(73) Assignee: Alberto Culver Company, Englewood Cliffs, NJ (US)

( * ) Notice: Subject to any disclaimer, the term of this patent is extended or adjusted under 35 U.S.C. 154(b) by 188 days.

(21) Appl. No.: 13/061,804

(22) PCT Filed: Sep. 3, 2009

(86) PCT No.: PCT/US2009/055873
§ 371 (c)(1),
(2), (4) Date: Apr. 15, 2011

(87) PCT Pub. No.: WO2010/028137
PCT Pub. Date: Mar. 11, 2010

(65) Prior Publication Data
US 2011/0180092 A1   Jul. 28, 2011

Related U.S. Application Data

(60) Provisional application No. 61/093,987, filed on Sep. 3, 2008.

(51) Int. Cl.
*A61Q 5/06* (2006.01)

(52) U.S. Cl.
USPC ........................................ 424/70.2; 424/70.11

(58) Field of Classification Search
None
See application file for complete search history.

(56) References Cited

U.S. PATENT DOCUMENTS

| | | | |
|---|---|---|---|
| 4,421,602 A | 12/1983 | Brunnmueller et al. | |
| 4,713,236 A | 12/1987 | Hoover et al. | |
| 4,992,267 A | 2/1991 | DenBeste et al. | |
| 5,478,553 A | 12/1995 | Chandran et al. | |
| 5,632,977 A | 5/1997 | Chandran et al. | |
| 5,989,534 A | 11/1999 | Samain | |
| 6,231,876 B1 | 5/2001 | Niessner et al. | |
| 6,271,327 B1 | 8/2001 | Niessner et al. | |
| 6,471,953 B1 | 10/2002 | N'Guyen et al. | |
| 6,589,510 B2 | 7/2003 | Kalbfleisch et al. | |
| 6,800,302 B2 | 10/2004 | Cannell et al. | |
| 2003/0185783 A1* | 10/2003 | Terazaki | 424/70.12 |
| 2003/0199642 A1 | 10/2003 | Schneider et al. | |
| 2006/0260632 A1 | 11/2006 | Campain | |
| 2007/0110690 A1 | 5/2007 | Nguyen et al. | |
| 2008/0182773 A1 | 7/2008 | Gauweiler et al. | |
| 2008/0260666 A1 | 10/2008 | Giroud et al. | |
| 2008/0274070 A1 | 11/2008 | Campain et al. | |
| 2009/0202465 A1 | 8/2009 | Mougin et al. | |
| 2009/0269295 A1 | 10/2009 | Benabdillah et al. | |
| 2010/0028280 A1* | 2/2010 | Philippe et al. | 424/70.2 |
| 2011/0048447 A1 | 3/2011 | Muller et al. | |
| 2011/0180092 A1 | 7/2011 | Verboom et al. | |
| 2011/0180093 A1 | 7/2011 | Verboom et al. | |
| 2011/0186070 A1 | 8/2011 | Verboom | |
| 2011/0192414 A1 | 8/2011 | Verboom et al. | |
| 2011/0192415 A1 | 8/2011 | Verboom et al. | |

FOREIGN PATENT DOCUMENTS

| | | |
|---|---|---|
| EP | 0 190 834 A2 | 8/1986 |
| EP | 0 524 346 A1 | 1/1993 |
| EP | 1 779 894 A1 | 5/2007 |
| EP | 1 977 731 A1 | 10/2008 |
| EP | 1 977 732 A1 | 10/2008 |
| EP | 2 149 363 A2 | 2/2010 |
| FR | 2887887 A1 | 1/2007 |
| FR | 2910274 A1 | 6/2008 |
| JP | 2002-255756 A | 9/2002 |
| WO | WO 89/04653 A1 | 6/1989 |
| WO | WO 02/15854 A1 | 2/2002 |
| WO | WO 2005/020943 A1 | 3/2005 |
| WO | WO 2007/003784 A1 | 1/2007 |
| WO | WO 2007/135299 A1 | 11/2007 |
| WO | WO 2009/079288 A1 | 6/2009 |
| WO | WO 2010/028137 A2 | 3/2010 |
| WO | WO 2010/028142 A2 | 3/2010 |
| WO | WO 2010/028143 A2 | 3/2010 |
| WO | WO 2010/028147 A2 | 3/2010 |
| WO | WO 2010/028153 A2 | 3/2010 |

OTHER PUBLICATIONS

"Lupamin 9095 High Molecular Weight Liner Polyvinylamine," basf, http://www2.basf.us/businesses/chemicals/performance/pdfs/Lupamin_9095.pdf, retrieved Jun. 15, 2011.

Syed et al., "Water-Soluble Polymers in Hair Care, Prevention and Repair of Damage during Hair Relaxing," *Water Soluble Polymers: Solution Properties and Applications*, Symposium, pp. 231-244 (Sep. 1997).

European Patent Office, International Search Report in International Application No. PCT/US2009/055895 (Jul. 4, 2011).

(Continued)

*Primary Examiner* — Jyothsna Venkat
(74) *Attorney, Agent, or Firm* — Ronald A. Koatz

(57) ABSTRACT

Provided is a method for styling mammalian hair that includes contacting the hair with a composition that includes a poly(vinylamine-vinylformamide) copolymer and a first carrier, contacting the hair with a composition that includes a citrate and a second carrier, and styling the hair. The method of the present invention promotes improved hair styling properties such as improved curl retention and straightness retention, e.g., under conditions of high relative humidity and temperature. The method can be used for semi-permanently straightening or curling the hair. Also provided is a method for controlling frizz by applying the copolymer and citrate compositions.

13 Claims, No Drawings

(56) References Cited

OTHER PUBLICATIONS

European Patent Office, International Preliminary Report on Patentability in International Application No. PCT/US2009/055895 (Jul. 28, 2011).

European Patent Office, International Search Report in International Application No. PCT/US2009/055880 (Jul. 15, 2011).

European Patent Office, International Preliminary Report on Patentability in International Application No. PCT/US2009/055880 (Jul. 28, 2011).

European Patent Office, International Search Report in International Application No. PCT/US2009/055886 (Sep. 23, 2011).

European Patent Office, International Preliminary Report on Patentability in International Application No. PCT/US2009/055886 (Oct. 13, 2011).

European Patent Office, International Search Report in International Application No. PCT/US2009/055882 (Sep. 23, 2011).

European Patent Office, International Preliminary Report on Patentability in International Application No. PCT/US2009/055882 (Oct. 13, 2011).

European Patent Office, International Search Report in International Application No. PCT/US2009/055873 (Sep. 30, 2011).

European Patent Office, International Preliminary Report on Patentability in International Application No. PCT/US2009/055873 (Sep. 30, 2011).

* cited by examiner

HAIR STYLING METHOD

BACKGROUND OF THE INVENTION

Hair styling or hair setting compositions are widely used by consumers in the cosmetic industry to retain a particular shape or style of the hair. Hair styling compositions can assist in manipulating or styling the hair, providing temporary benefits in holding the shape of the hairstyle (fixing) and/or maintaining the shine or appearance (grooming, restyling) of the hair, e.g., in the evening, during the day, between hair washing periods, or between subsequent hair setting procedures.

Various methods are used to measure the efficacy of a hair-styling composition. One method commonly employed to objectively test the efficacy of hair styling compositions involves measuring curl retention under humid conditions. Another method involves semi-permanent hair straightening using a flat iron followed by several wash-out steps. Additional methods of subjective evaluation may be employed that include, for examples: visual and tactile sensory methods (e.g., by visual examination and touching) for characteristics such as appearance (shine, cleanliness, naturalness of appearance and texture), feel (stiffness, tackiness, softness), curl memory (bounce, and restylability), straightness memory (flatness), ease of combing and brushing the hair, residue (flaking), static, smoothness, and the like. Also of importance are the aesthetic characteristics and appearance provided by hair styling compositions before, during, and after application to hair. Preferably, the product viscosity should be non-runny to avoid dripping during application. The product should be easy to spread, have a smooth texture, a non-tacky feel, and be able to dry relatively quickly on the hair.

Of further importance is the ability of hair styling compositions to control hair "frizz," which generally causes hair to become unmanageable and appear undisciplined. Frizz can become a problem when hair is exposed to higher humidity, e.g., a relative humidity of about 80% or more. The problem can worsen in people with curly hair, either naturally or "permed," leading to what many have termed a "bad hair day." In such a case, hair loses its natural shape and/or its curl definition. Hair is often subjected to a wide variety of stresses that can cause damage to the hair, resulting in frizz. These include shampooing, rinsing, drying, heating, combing, styling, perming, coloring, exposure to the elements, and the like. Such stresses can leave the hair in a dry, rough, lusterless, or frizzy condition, which can be caused, e.g., by repeated abrasion of the hair surface and removal of the hair's natural oils and other natural conditioning and moisturizing components. Additionally, hair is often subjected to weather-related stresses, e.g., sunlight, wind, and changes in temperature and humidity, which can cause hair frizz and other conditions considered by consumers to be cosmetically undesirable.

Hair-setting compositions that include one or more hair-setting polymers to impart styling and/or fixative properties have been disclosed. For example, U.S. Pat. No. 4,713,236 describes compositions that include amine-containing polymers and copolymers that contain a primary pendant amine group, for imparting conditioning properties to hair. U.S. Pat. Nos. 5,478,553 and 5,632,977 describe hair fixative compositions containing polymeric n-vinyl formamide and methods of treating hair. U.S. Pat. No. 6,800,302 describes compositions comprising hydrocarbon substituted monosaccharides that can be heat activated for durable non-permanent shaping of keratinous fibers. U.S. Published Patent Application No. 2007/0110690 describes a process for inhibiting hair from becoming frizzy that involves contacting hair with anionic silicone and with polyvinylamine.

Providing hair styling compositions that exhibit good high humidity curl and/or straightness retention while maintaining desirable subjective properties, e.g., smooth texture, curl memory, bounce, naturalness of appearance, etc., has been difficult to achieve with conventional hair-setting compositions. There is an ongoing need for hair styling compositions that provide high humidity curl and/or straightness retention and resistance to frizziness, as well as desirable subjective properties. The present invention provides such compositions and associated methods of use.

BRIEF SUMMARY OF THE INVENTION

The present invention provides a method for styling mammalian hair, which method includes contacting the hair with a styling-effective amount of a composition comprising a poly(vinylamine-vinylformamide) copolymer and a first carrier, and a composition comprising a styling-effective amount of a citrate and a second carrier. The treated hair is then styled.

The present invention also provides a method for controlling frizz in mammalian hair, which method includes contacting the hair with a frizz-controlling effective amount of a composition comprising a poly(vinylamine-vinylformamide) copolymer and a first carrier, and a composition comprising a frizz-controlling effective amount of a citrate and a second carrier. The tendency for the treated hair to exhibit frizz is thereby reduced, and the treated hair optionally can be styled.

DETAILED DESCRIPTION OF THE INVENTION

In accordance with the present invention, keratinous fibers such as mammalian (e.g., human) hair are treated with a composition that includes an effective amount of one or more poly(vinylamine-vinylformamide) copolymers and a first carrier, and a composition that includes an effective amount of a citrate and a second carrier. The effective amounts used preferably include amounts that are effective to retain hair-styling, such as e.g., curl retention or straightness retention, through at least three washing cycles. Preferably the carriers used in either composition are aqueous carriers. The compositions used in accordance with the methods of the present invention also provide hair that exhibits good frizz control under conditions of high relative humidity. The poly(vinylamine-vinylformamide) copolymer composition and citrate compositions may be applied together or in any order. The hair can be contacted with either composition, the poly(vinylamine-vinylformamide) copolymer composition and/or the citrate compositions, for any effective amount of time, e.g. from about 1 minute to about 30 minutes, from about 1 minutes to about 20 minutes, or from about 5 minutes to about 10 minutes. In some embodiments, the treated hair is rinsed with water. In some embodiments, the treated hair has heat applied in an amount effective to at least semi-permanently style the hair, e.g., to provide curl retention or straightness retention in the styled hair after at least three washing cycles. The heat can be applied under conditions set forth in greater detail below. The treated hair can then be styled using any suitable method, including conventional styling methods. In preferred embodiments, the poly(vinylamine-vinylformamide) copolymer composition is first applied to the hair, and the citrate composition is applied to the hair thereafter, i.e., following application of the poly(vinylamine-vinylformamide) copolymer composition.

The citrate composition used in accordance with the method of the present invention preferably includes a citrate salt such as, e.g., disodium citrate. Other citrate compounds with the scope of the citrate composition also may include salts that contain the citrate $(C_3H_5O(COO)_3^{-3})$ ion, sodium citrate, trisodium citrate, acid salts that contain the hydrogen or dihydrogen citrate ions, and combinations or mixtures thereof. Citrate salts with potassium and calcium can suitably be used in the composition. Disodium citrate is a particularly preferred salt.

The poly(vinylamine-vinylformamide) copolymer composition used in accordance with the method of the present invention can have a pH of from about 4 to about 9, e.g., a pH of from about 6 to about 9, e.g., a pH of from about 7 to about 9, e.g., a pH of from about 8 to about 9. In some embodiments, the poly(vinylamine-vinylformamide) copolymer composition used in accordance with the method of the present invention desirably has a pH of from about 6 to about 9.

The citrate composition preferably has a pH of from about 3 to about 8, e.g., a pH of from about 4 to about 7, e.g., a pH of from about 5 to about 6. In some embodiments, the citrate composition used in accordance with the method of the present invention desirably has a pH of from about 5 to about 6, e.g., in some embodiments the citrate composition utilizes disodium citrate as the citrate component at a pH of from about 5 to about 6. If desired, the solution pH may be adjusted using one or more weak organic acids (e.g., citric acid) and/or one or more mineral acids.

The poly(vinylamine-vinylformamide) copolymer composition used in accordance with the method of present invention preferably includes one or more poly(vinylamine-vinylformamide) copolymers as a styling polymer. In some embodiments, the composition used in accordance with the method of the present invention can include one or more linear poly(vinylamine-vinylformamide) copolymers, a polyvinylpyrrolidone polymer, and an aqueous carrier. The poly(vinylamine-vinylformamide) copolymer is preferably present in the composition in a hair-styling effective amount, e.g., in an amount effective to promote at least about 50% curl retention in the hair after about 2 hours under conditions of about 90% relative humidity and a temperature about 75° F. [24° C.], when the composition is applied to mammalian hair. Suitable poly(vinylamine-vinylformamide) copolymers can be obtained, e.g., by partial hydrolysis of a polyvinylformamide, to produce one or more copolymers that contain vinylamine and vinylformamide monomeric units. Poly(vinylamine-vinylformamide) copolymers, which can be used as a styling polymer in the composition, include the polymers contained in products sold under the trademark LUPAMIN®, which are sold by BASF and are supplied as aqueous solutions containing linear poly(vinylamine-vinylformamide) copolymers. The polymers in LUPAMIN® are prepared by polymerization of vinylformamide followed by partial hydrolysis of the polyvinylformamide. Exemplary poly(vinylamine-vinylformamide) copolymers, which can be used in the composition, include the polymers contained in LUPAMIN® 9095, LUPAMIN® 9050, LUPAMIN® 9030, LUPAMIN® 9010, LUPAMIN® 5095, and LUPAMIN® 1595.

The digits used in conjunction with the LUPAMIN® product name correspond to the molecular weight and the extent of hydrolysis of the polymer. The first two (i.e., first and second) digits in the product name correspond to the polymer molecular weight. For instance, the first two digits in LUPAMIN® 9095, LUPAMIN® 9050, LUPAMIN® 9030 and LUPAMIN® 9010, i.e., "90," are indicative of the molecular weight of the polymer. The average molecular weights of exemplary polymers and other properties associated with corresponding LUPAMIN® products, as published in BASF's technical bulletins, are summarized below in Table A.

TABLE A

|  | Lupamin ® 9095 | Lupamin ® 9030 | Lupamin ® 9010 | Lupamin ® 5095 | Lupamin ® 1595 |
| --- | --- | --- | --- | --- | --- |
| Form | Liquid | Liquid | Liquid | Clear Pale Yellow Liquid | Clear Pale Yellow Liquid |
| Density (g/mL) | 1.08 | 1.08 | 1.08 | 1.08 | 1.08 |
| % Solids (wt %) | 20-22% | 16-18% | 13-15% | 21-24% | 28-32% |
| % Polymer (wt %) | 6-8 | 10-12 | 12-14* | 8-12 | 9-11 |
| Ave. Molecular Weight (g/mol) | 340,000 | 340,000 | 340,000 | 45,000 | <10,000 |
| Viscosity (mPas at 20° C.) | >5000 | <5000 | <5000 | <1000 | <1000 |
| pH | 7-9 | 7-9 | 7-9 | 7-9 | 7-9 |

*estimated based on solids content, hydrolysis index and polymer content relative to total solids reported for other LUPAMIN ® products LUPAMIN® 9050 is believed to have a molecular weight of 340,000 based on the molecular weights reported in BASF's technical bulletins for LUPAMIN® 9095, 9030 and 9010. LUPAMIN® 9050 is believed to have a solids content of about 16-19 wt % based on the results of solids testing performed on a product sample and solids content reported for LUPAMIN® 9095, 9030 and 9010. LUPAMIN® 9050 is estimated to have a poly(vinylamine-vinylformamide) copolymer content (i.e., polymer content) of about 9-12 wt % based on solids testing, and reported solids and polymer content for other LUPAMIN® products.

The last two (i.e., third and fourth) digits used in conjunction with the LUPAMIN® product name represent the degree of hydrolysis, which corresponds to the percent of the formamide functional groups in the polymer that have been hydrolyzed and converted into vinylamine units. For instance, the last two digits in LUPAMIN® 9095, i.e., "95," indicate the degree of hydrolysis, i.e., that the polymer is about 95% hydrolyzed (or greater than 90% hydrolyzed as noted in BASF's technical bulletins for Lupamin® 5095 and Lupamin® 1595). Thus, the polymers contained in LUPAMIN® 9095, LUPAMIN® 5095, and LUPAMIN® 1595 are believed to contain about 95% vinylamine monomeric units (vinylamine monomers) and about 5% vinylformamide monomeric units (vinylformamide monomers). By contrast, LUPAMIN® 9050 is believed to contain about 50% vinylamine monomers and about 50% vinylformamide monomers, LUPAMIN® 9030 is believed to contain about 30% vinylamine monomers and about 70% vinylformamide monomers, and LUPAMIN® 9010 is believed to contain about 10% vinylamine monomers and about 90% vinylformamide monomers.

The poly(vinylamine-vinylformamide) copolymer composition used in accordance with the method of the present invention also can include two or more poly(vinylamine-vinylformamide) copolymers. In some embodiments, combinations of two or more poly(vinylamine-vinylformamide) copolymers have been found to promote unexpectedly superior high humidity curl retention properties. In one embodiment, the composition used in accordance with the method of the present invention includes at least one high molecular weight poly(vinylamine-vinylformamide) copolymer and at least one low molecular weight poly(vinylamine-vinylformamide) copolymer. As used herein, a high molecular weight poly(vinylamine-vinylformamide) copolymer refers to a poly(vinylamine-vinylformamide) copolymer with an average molecular weight greater than about 100,000 g/mole and a low molecular weight poly(vinylamine-vinylformamide) copolymer refers to a poly(vinylamine-vinylformamide) copolymer with an average molecular weight of about 100,000 g/mole or less.

The high molecular weight poly(vinylamine-vinylformamide) copolymer can include, e.g., at most about 95% vinylamine monomers (e.g., about 95% vinylamine monomers and about 5% vinylformamide monomers), at most about 50% vinylamine monomers (e.g., about 50% vinylamine monomers and about 50% vinylformamide monomers), at most about 30% vinylamine monomers (e.g., about 30% vinylamine monomers and about 70% vinylformamide monomers), or at most about 10% vinylamine monomers (e.g., about 10% vinylamine monomers and about 90% vinylformamide monomers). Suitable high molecular weight poly(vinylamine-vinylformamide) copolymers include, for example, LUPAMIN® 9095, LUPAMIN® 9050, LUPAMIN® 9030, and LUPAMIN® 9010 polymers. The low molecular weight poly(vinylamine-vinylformamide) copolymer can include, e.g., at most about 95% vinylamine monomers (e.g., about 95% vinylamine monomers and about 5% vinylformamide monomers). Suitable low molecular weight poly(vinylamine-vinylformamide) copolymers include, e.g., LUPAMIN® 5095 and LUPAMIN® 1595 polymers.

The poly(vinylamine-vinylformamide) copolymer can be present in the poly(vinylamine-vinylformamide) copolymer composition in an amount of, e.g., from about 0.01 wt % to about 90 wt %, e.g., from about 0.01 wt % to about 50 wt %, e.g., from about 0.01 wt % to about 30 wt %, e.g., from about 0.01 wt % to about 20 wt %, e.g., from about 0.01 wt % to about 10 wt %, e.g., from about 0.1 wt % to about 10 wt %, e.g., from about 0.1 wt % to about 5 wt %, e.g., from about 0.1 wt % to about 4 wt %, e.g., from about 0.1 wt % to about 3 wt %, e.g., from about 0.1 wt % to about 2 wt %, e.g., from about 1 wt % to about 2 wt %, based on the total weight of the composition. In some embodiments, the poly(vinylamine-vinylformamide) copolymer composition contains from about 1 wt % to about 2 wt % of one or more poly(vinylamine-vinylformamide) copolymers, based on the total weight of the composition. In some embodiments, the poly(vinylamine-vinylformamide) copolymer composition utilizes LUPAMIN® 9095 as the poly(vinylamine-vinylformamide) copolymer.

The citrate compound(s) in the citrate composition can be present in an amount of, e.g., from about 0.1 wt % to about 15 wt %, e.g., in an amount of from about 0.1 wt % to about 12 wt %, e.g., from about 1 wt % to about 12 wt %, e.g., from about 1 wt % to about 10 wt %, e.g., from about 2 wt % to about 10 wt %, e.g., from about 3 wt % to about 10 wt %, e.g., from about 4 wt % to about 10 wt %, e.g., from about 5 wt % to about 10 wt %, e.g., from about 5 wt % to about 9 wt %, e.g., from about 5 wt % to about 8 wt %, e.g., from about 5 wt % to about 7 wt %, e.g., about 6 wt %, based on the total weight of the citrate composition. In some embodiments, the citrate used in the citrate composition is a mixture of citric acid and a citric acid salt such as, e.g., disodium citrate.

Either composition, i.e., the poly(vinylamine-vinylformamide) copolymer composition and/or the citrate composition, used in accordance with the method of the present invention can include polyvinylpyrrolidone (PVP), which has been found to provide the hair with good styling performance and desirable subjective properties such as, e.g., gloss, low flaking and smooth texture, without sacrificing high humidity curl retention or resistance to fizz. The composition can include polyvinylpyrrolidone, e.g., in an amount of from about 0.01 wt % to about 20 wt % polyvinylpyrrolidone, from about 0.05 wt % to about 15 wt % polyvinylpyrrolidone, from about 0.1 wt % to about 10 wt % polyvinylpyrrolidone, from about 0.1 wt % to about 5 wt % polyvinylpyrrolidone, from about 0.1 wt % to about 1 wt % polyvinylpyrrolidone, or from about 0.5 wt % to about 1 wt % polyvinylpyrrolidone.

Either composition used in accordance with the method of the present invention can further include one or more additional ingredients such as, for example, a conditioning agent, a film former or modifier (in addition to PVP), a thickener, a surfactant, an emollient, an emulsifier, a propellant, a fatty alcohol, and the like, and combinations thereof. The composition preferably exists in the form of a mousse or a gel.

Suitable additional film formers beyond PVP can include, e.g., vinylpyrrolidone copolymers, cationic cellulose derivatives, polyurethanes, acrylates/hydroxyester acrylate copolymer, celluloses and polysaccharide gums and their derivatives and the like, and combinations thereof. The composition used in accordance with the method of the present invention can include, for example, from about 0.01 wt % to about 10 wt % of one or more additional film formers, from about 0.05 wt % to about 5 wt % of one or more additional film formers, or from about 0.1 wt % to about 5 wt % of one or more additional film formers. Suitable film forming polymers also can include, e.g., one or more nonionic copolymers of N-vinylpyrrolidone, methacrylamide and N-vinylimidazole.

Suitable film forming polymers also can include, e.g., one or more copolymers of vinylpyrrolidone and dimethylaminoethyl methacrylate(s). The composition used in accordance with the method of the present invention can include, e.g., from about 0.01 wt % to about 15 wt % of one or more film forming vinylpyrrolidone copolymers, e.g., from about 0.05 wt % to about 10 wt % of one or more film forming vinylpyrrolidone copolymers, or from about 0.1 wt % to about 10 wt % of one or more film forming vinylpyrrolidone copolymers. Exemplary film forming vinylpyrrolidone copolymers include LUVISET® CLEAR, available from BASF, and VP/dimethylaminoethyl methacrylate copolymer 845-G, available from International Specialty Products.

Suitable film formers further can include, e.g., cationic cellulose derivatives. The composition can include, for example, from about 0.01 wt % to about 10 wt % of one or more cationic cellulose derivatives, from about 0.02 wt % to about 5 wt % of one or more cationic cellulose derivatives, or from about 0.05 wt % to about 5 wt % of one or more cationic cellulose derivatives. A preferred class of cationic cellulose derivatives includes copolymers of a hydroxyethylcellulose and diallyldimethyl ammonium chloride. An exemplary cationic cellulose derivative is polyquaternium-4, a copolymer of cellulose, 2-hydroxyethyl ether and diallyldimethyl ammonium chloride. Polyquaternium-4 is the active ingredient in products marketed under the names CELQUAT® H-100 and CELQUAT® L-200, available from Akzo Nobel.

It will be appreciated that some film formers, e.g., CELQUAT® H-100 also may function as conditioning agents.

Suitable film modifiers can include, for example, one or more aminosilicones, one or more PEG-n dimethicones, one or more PEG-n/PPG-n dimethicones, one or more cyclomethicones, one or more plasticizers (e.g., glycols, glycol ethers, glycerine), and the like, and combinations thereof. Suitable dimethicones can include polyethylene/propylene glycol derivatives of dimethicone containing an average of n moles of ethylene/propylene oxide, e.g., where n is in the range of about 3 to about 20. An exemplary PEG-n/PPG-n dimethicone includes a PEG-18/PPG-18 dimethicone, available from Dow Corning under the trade name DC-190. The composition used in accordance with the method of the present invention can include, e.g., from about 0.01 wt % to about 10 wt % of one or more film modifiers, from about 0.02 wt % to about 5 wt % of one or more film modifiers, or from about 0.05 wt % to about 5 wt % of one or more film modifiers.

Suitable thickeners can include, e.g., one or more associative and non-associative thickeners, one or more polysaccharides, polysaccharide derivatives, gums (e.g., guar gum, xanthan gum), and the like, and combinations thereof. Suitable associative thickeners can include, e.g., acrylates/beheneth-25 acrylate copolymers, polyether-1/1,3-butylene glycol blends, and combinations thereof. The composition used in accordance with the method of the present invention can include, for example, from about 0.01 wt % to about 15 wt % of one or more thickeners, from about 0.05 wt % to about 8.0 wt % of one or more thickeners, or from about 0.1 wt % to about 3.0 wt % of one or more thickeners. Exemplary thickeners include TINOVIS® GTC, available from Ciba Specialty Chemicals, PURE THIX® HH, available from Southern Clay, and combinations thereof.

Suitable fatty alcohols in either composition used in accordance with the method of the present invention can include linear or branched, saturated or unsaturated $C_8$-$C_{24}$ fatty alcohol. The fatty alcohols can be selected from the group consisting of myristyl alcohol, cetyl alcohol, stearyl alcohol, oleyl alcohol, behenyl alcohol, or the like, and mixtures thereof. The fatty alcohols can be present in any suitable amount.

Suitable emulsifiers in either composition used in accordance with the method of the present invention can include stearamidopropyl dimethylamine, glyceryl esters, particularly those with an HLB value of about 3 to about 4, for example, about 3.5 to about 4.0 (such as glyceryl stearate), or the like, and mixtures thereof. The emulsifier can be present in any suitable amount.

The carriers in either composition used in accordance with the method of the present invention can comprise any suitable carriers. Preferably the carriers are aqueous carriers that can include any suitable quantity of water, e.g., from about 25 wt % to about 97 wt % water (e.g., from about 30% to about 95% water). Preferably, the composition includes from about 50 wt % to about 97 wt %, and more preferably from about 70 wt % to about 90 wt %, and most preferably from about 80 wt % to about 90 wt % water. Preferably, the water used in the composition is deionized water.

Suitable conditioning agents can include, for example, one or more amphoteric copolymers, one or more amphoteric terpolymers, one or more cationic conditioners and the like, and combinations thereof. Suitable conditioning agents can include amphoteric terpolymers of acrylic acid, diallyl dimethyl ammonium chloride, and acrylamide. Suitable conditioning agents can include monoalkyl trimonium salts wherein the long-chain monoalkyl groups contain about eight or more carbons such as, e.g., cetrimonium chloride or cocotrimonium chloride. Cocotrimonium chloride is also known as cocoalkyltrimethyl ammonium chloride and is commercially available as ARQUAD® C-33W from Akzo Nobel. Either composition used in accordance with the method of the present invention can include, for example, from about 0.01 wt % to about 20 wt % of one or more conditioning agents, from about 0.01 wt % to about 15 wt % of one or more conditioning agents, or from about 0.05 wt % to about 10 wt % of one or more conditioning agents. In some embodiments, the conditioning agent can be present in the composition, e.g., in an amount of from about 0.25 wt % to about 3 wt %, from about 0.5 wt % to about 2 wt %, or from about 0.70 wt % to about 1.5 wt %. An exemplary conditioning agent is polyquaternium-39, sold under the tradename MERQUAT® PLUS 3330, available from Nalco Co. Other exemplary products that may serve as conditioning agents include polyquaternium-4 and/or VP/dimethylaminoethyl methacrylate copolymer 845-G. For example, in some embodiments the poly(vinylamine-vinylformamide) copolymer composition includes from about 0.33 wt % to about 1.5 wt % cocotrimonium chloride and in some embodiments the citrate composition includes about 0.25 wt % to about 1.25 wt % cetrimonium chloride.

Suitable surfactants can include, e.g., one or more anionic, nonionic, cationic, and amphoteric surfactants, with nonionic, cationic, and amphoteric surfactants being preferred. Exemplary surfactants include PPG-5/Ceteth 20, Oleth-20, polysorbate-20, and cocamidopropyl betaine. The composition used in accordance with the method of the present invention can include, for example, from about 0.01 wt % to about 20 wt % of one or more surfactants, from about 0.01 wt % to about 15 wt % of one or more surfactants, or from about 0.05 wt % to about 10 wt % of one or more surfactants.

Either composition used in accordance with the method of the present invention can include other components that may be suitable for use in conventional hair styling compositions such as, e.g., conventional hair fixative, hair setting and/or hair grooming gels, rinses, emulsions (oil-in-water, water-in-oil or multiphase), lotions, creams, pomades, sprays (pressurized or non-pressurized), spritzes, mousses, foams, conditioners, and solids (e.g., as sticks, semisolids and the like).

If desired, either composition used in accordance with the method of the present invention can include a propellant, e.g., for dispensing the composition (e.g., in the form of a mousse or gel). The composition can include, for example, from about 0.01 wt % to about 20 wt % of one or more propellants, from about 0.01 wt % to about 15 wt % of one or more propellants, or from about 0.05 wt % to about 10 wt % of one or more propellants. Exemplary propellants include propane, butane, and mixtures thereof.

In some embodiments, the hair-styling method of the present invention exhibits at least semi-permanent hair straightening after at least about three wash cycles comprising shampoo and conditioner treatments and after exposure for over about 12 hours to a high humidity environment, which environment may be operated at conditions including 90% Relative Humidity and a temperature of about 75° F. [24° C.].

In accordance with the method of the present invention, the keratinous fibers may be styled in any suitable manner. In addition, the composition can be applied in any suitable manner, e.g., by working the composition through the hair, e.g., with the hands and fingers or with a suitable implement such as, e.g., a comb or brush, to ensure uniform coverage. In some embodiments, the hair may be rinsed with water after applying either or both compositions and an additional conditioner composition may be optionally contacted with the hair before drying or shaping steps.

In accordance with some embodiments of the present invention, heat is applied to hair treated with the composition comprising the poly(vinylamine-vinylformamide) copolymer and the citrate composition. The heat is applied in amount effective to at least semi-permanently style the hair, and the hair is accordingly styled at least semi-permanently. An effective amount of heat may be applied by contacting the hair with a styling device (e.g., a flat iron, curling iron, curlers, etc.) at a temperature (e.g., the surface temperature of the portion of the device that contacts the hair) of at least about 100° C. for an effective time period. If a styling device is used, the temperature of the device preferably ranges from about 190° C. to about 240° C., from about 200° C. to about 240° C., or from about 210° C. to about 240° C. In some embodiments, heat is applied to the hair with a styling device at a temperature of about 225° C. [438° F.]. The heat can be applied for an effective time period, for example, by contacting a section of hair with a device for an appropriate length of time (e.g., for at least about 1 second). The heat also can be applied for an effective time period, for example, by passing or drawing a device (e.g., a flat iron) through a section of hair (e.g., lengthwise, e.g., with a combing motion through the hair while the styling surface of the device remains in contact with at least a portion of the hair during each pass) at an appropriate rate, e.g., for from about 2 seconds to about 10 seconds. It will be appreciated that the time period required for contacting the hair with a heat-styling device, to semi-permanently style hair in accordance with the invention, can depend on a number of factors. Such factors can include, e.g., the nature and extent of chemical treatment on the hair, the type and condition of hair involved, the length of the hair (which, of course, may impact the rate and length of time required for each pass for certain styling devices), the temperature of the device, the nature of the device, and other factors. A suitable heat-styling method is disclosed in US 2007/0280896, which discloses a method for straightening hair by passing a flat iron at 193° C. over the hair three times for 6-7 seconds each pass.

The styling can thus include contacting the hair with a shaped surface so as to manipulate the hair to conform to the shape of the surface. If desired, heat can be applied directly to the hair by contacting the hair with a heated shaped surface, which can also be used to style and manipulate the hair to conform to the shape of the surface. Thus, in some embodiments, the shaped surface is heated and the heat is applied to the hair with the shaped surface. If desired, the heat application and styling can be performed simultaneously. Heat can also be applied via an indirect heat source such as, for example, blow dryers, hood dryers, hating caps, steamers, and combinations thereof. In some embodiments, it can be desirable to use a combination of direct and indirect heat sources. When using a shaped surface, a straight surface may be used for straightening hair and a curved surface may be used for curling hair, or a combination of such surfaces may be used, if desired. Preferably, the heat can be applied in multiple stages or passes. Such stages or passes can include applying heat to the hair and styling as described herein at least two times, e.g., so as to apply heat and to manipulate the hair to conform to the shape of a surface with intermediate removal of the heat source between stages or passes. Thus, in some embodiments, the heat application and styling are performed two or more times. In other embodiments, the heat application and styling are performed three or more times. For example, when using a flat iron to straightening the hair, two passes of the iron over (against) the hair can be performed, and in some instances three passes of the iron over (against) the hair can be performed.

The present invention further provides a method of controlling frizz, which preferably includes applying to mammalian hair a frizz-controlling effective amount of a composition that includes one or more poly(vinylamine-vinylformamide) copolymers and a first carrier and a composition that includes citrate and a second carrier. Consumers often associate frizz, e.g., the tendency of individual hairs to stray from alignment or conformity with one another, with an unruly or undesirable appearance. The styling compositions used in accordance with the methods of the present invention can be use to effectively control (e.g., inhibit, reduce or ameliorate) frizz in mammalian hair.

The following examples further illustrate the invention but, of course, should not be construed as in any way limiting its scope.

EXAMPLE 1

This example illustrates a composition comprising a poly(vinylamine-vinylformamide) copolymer and an aqueous carrier. A solution was prepared that contained 86.48 wt % distilled water, 0.52 wt % citric acid, 0.5 wt % stearamidopropyldimethylamine, 2 wt % cetyl alcohol, and 10 wt % Lupamin® 9095. First, the citric acid was added to the distilled water and heated up to 80° C. Next the stearamidopropyldimethylamine and the cetyl alcohol were added to the solution and mixed for about ten minutes. The mixed solution was cooled down to about 65° C. and the Lupamin® 9095 was added to form a composition comprising a poly(vinylamine-vinylformamide) copolymer and an aqueous carrier, i.e. the "LUPAMIN® 9095 Solution."

EXAMPLE 2

This example illustrates a citrate composition comprising a citrate and an aqueous carrier. A solution was prepared that contained about 3 wt % disodium citrate. Some of the commercial disodium citrate used also contained monocitrate and tricitrate along with a small amount of citric acid. About 1 gram of citric acid (50 wt %) was combined with about 2.5 grams citrate and 46.5 grams of distilled water to form the sodium tricitrate solution.

EXAMPLE 3

This example demonstrates a method for styling hair. In this example, a screening method for semi-permanent hair straightening 1 inch [2.5 cm] tresses was conducted in three phases, which included (1) pre-cleansing tresses, (2) applying a hair-straightening treatment of two compositions, and (3) washing out the tresses.

In the first phase, ten dry curly hair tresses were obtained from International Hair Importers. The hair tresses were formed into 8 inch [20.3 cm] lengths cut in 1 inch [2.5 cm] wide swatches. The tresses were rinsed with warm tap water at approximately 35-40° C. flowing at about 0.7 gallons/minute [2650 cc/minute] for ten seconds. The tress was rinsed again 30 seconds and then excess water was squeezed out. The tresses were towel dried with cleaning tissues such as KIMWIPES.

In the second phase, the tresses were contacted with a composition comprising a poly(vinylamine-vinylformamide) copolymer and an aqueous carrier. The composition was massaged in with fingers and then combed through twice with large teeth and then twice with small teeth of a two-sided comb. The composition was left on the hair tress for a fixed time period and then excess solution was squeezed out. Next, the tresses were contacted with a citrate composition. The citrate composition was massaged in with fingers and then combed through twice with large teeth and then twice with small teeth of a two-sided comb. The citrate composition was left on the hair tress for another fixed time period and then excess solution was squeegeed out.

After contacting the hair tresses with the compositions, the tresses were blown dry until the hair was almost dry and the hair was combed down. A flat iron was applied to the hair tress at a temperature of about 438° F. [225° C.] with two passes at a rate of about 10 seconds per pass with a combing stroke after each pass. Then the hair fibers were detangled by combing through the whole tress, and the flat iron was applied again with two more passes with a comb through after each pass in order to obtain styled and straightened hair tresses. The hair tresses were then allowed to hang for a set time period.

In the third phase, the straightened hair tresses were wetted out with warm tap water at approximately 35-40° C. flowing at about 0.7 gallons/minute [2650 cc/minute] for ten seconds. Then about 2 cc of a commercial shampoo was applied and distributed onto the tresses from top to bottom rubbing the product down and up three times on each side (front/back) with about a 1 minute contact time. The tresses were placed in the palm on one hand and then rinsed for about 30 seconds. Similarly, about 2 cc of a commercial conditioner was applied onto the tresses from top to bottom and distributed by rubbing the conditioner down and up three times on each side (front/back) with about a 1 minute contact time. The tresses were rinsed again for about 30 seconds under warm tap water and then excess water was squeezed out. The tresses were then combed through once with large teeth and then once with small teeth of a two-sided comb. The tresses were then hung to air-dry.

The method using the two compositions resulted in improved hair styling and maintained straighter hair throughout the screening method as compared to the control hair tresses that were not exposed to the citrate solution.

EXAMPLE 4

This example demonstrates another method for styling hair. In this example, a method for semi-permanent hair straightening 1 inch [2.5 cm] tresses was conducted in three phases, which included (1) pre-cleansing tresses, (2) applying a hair-straightening treatment of two compositions comprising conditioning agents, and (3) washing out the tresses.

In the first phase, dry curly hair tresses were obtained from International Hair Importers. The hair tresses were formed into 8 inch [20.3 cm] lengths cut in 1 inch [2.5 cm] wide swatches. The tresses were rinsed with warm tap water at approximately 35-40° C. flowing at about 0.7 gallons/minute [2650 cc/minute] for ten seconds. The tress was rinsed again for 30 seconds and then excess water was squeezed out. The tresses were towel dried with cleaning tissues such as KIM-WIPES.

In the second phase, the tresses were contacted with a composition containing about 10 wt % of Lupamin® 9095 solution, about 3 wt % of Arquad® C-33W solution (containing about 33 wt % cocotrimonium chloride) and the balance being an aqueous carrier. The composition was massaged in with fingers and then combed through twice with large teeth and then twice with small teeth of a two-sided comb. The composition was left on the hair tress for about ten minutes and then excess solution was squeezed out. Next, the tresses were contacted with a citrate composition containing about 1 wt % citric acid, about 5 wt % sodium citrate, about 0.75 wt % of cetrimonium chloride, and the balance being an aqueous carrier. The citrate composition was massaged in with fingers and then combed through twice with large teeth and then twice with small teeth of a two-sided comb. The citrate composition was left on the hair tress for about two minutes and then excess solution was squeegeed out.

After contacting the hair tresses with the compositions the tresses were rinsed with water for about three minutes and then the tresses were blown dry until the hair was almost about 80% dry (i.e. no free moisture) and the hair was combed down. A flat iron was applied to the hair tress at a temperature of about 438° F. [225° C.] with two passes at a rate of about 10 seconds per pass with a combing stroke after each pass. Then the hair fibers were detangled by combing through the whole tress, and the flat iron was applied again with two more passes with a comb through after each pass in order to obtain styled and straightened hair tresses. The hair tresses were then allowed to hang for a set time period.

In the third phase, the straightened hair tresses were wetted out with warm tap water at approximately 35-40° C. flowing at about 0.7 gallons/minute [2650 cc/minute] for ten seconds. Then about 2 cc of a commercial shampoo was applied and distributed onto the tresses from top to bottom rubbing the product down and up three times on each side (front/back) with about a 1 minute contact time. The tresses were placed in the palm on one hand and then rinsed for about 30 seconds. Similarly, about 2 cc of a commercial conditioner was applied onto the tresses from top to bottom and distributed by rubbing the conditioner down and up three times on each side (front/back) with about a 1 minute contact time. The tresses were rinsed again for about 30 seconds under warm tap water and then excess water was squeezed out. The tresses were then combed through once with large teeth and then once with small teeth of a two-sided comb. The tresses were then hung to air-dry.

The method using the poly(vinylamine-vinylformamide) copolymer composition with a conditioning agent and the citrate composition with a conditioning agent resulted in improved hair styling with hair that felt natural and was easy to comb, straighten, and wash.

EXAMPLE 5

This example demonstrates another method for styling hair. In this example, a method for semi-permanent hair straightening 1 inch [2.5 cm] tresses was conducted in three phases, which included (1) pre-cleansing tresses, (2) applying a hair-straightening treatment of two compositions comprising conditioning agents, and (3) washing out the tresses.

In the first phase, dry curly hair tresses were obtained from International Hair Importers. The hair tresses were formed into 8 inch [20.3 cm] lengths cut in 1 inch [2.5 cm] wide swatches. The tresses were rinsed with warm tap water at approximately 35-40° C. flowing at about 0.7 gallons/minute [2650 cc/minute] for ten seconds. The tress was rinsed again for 30 seconds and then excess water was squeezed out. The tresses were towel dried with cleaning tissues such as KIM-WIPES.

In the second phase, the tresses were contacted with a composition containing about 10 wt % of Lupamin® 9095 solution, about 4 wt % of Arquad® C-33W solution (containing about 33 wt % cocotrimonium chloride) and the balance being an aqueous carrier. The composition was massaged in with fingers and then combed through twice with large teeth and then twice with small teeth of a two-sided comb. The composition was left on the hair tress for about ten minutes and then excess solution was squeezed out. Next, the tresses were contacted with a citrate composition containing about 1 wt % citric acid, about 5 wt % sodium citrate, about 1 wt % of cetrimonium chloride, and the balance being an aqueous carrier. The citrate composition was massaged in with fingers and then combed through twice with large teeth and then twice with small teeth of a two-sided comb. The citrate composition was left on the hair tress for about two minutes and then excess solution was squeegeed out.

After contacting the hair tresses with the compositions the tresses were rinsed with water for about three minutes and then the tresses were blown dry until the hair was almost about 80% dry (i.e. no free moisture) and the hair was combed down. A flat iron was applied to the hair tress at a temperature of about 438° F. [225° C.] with two passes at a rate of about 10 seconds per pass with a combing stroke after each pass. Then the hair fibers were detangled by combing through the whole tress, and the flat iron was applied again with two more passes with a comb through after each pass in order to obtain styled and straightened hair tresses. The hair tresses were then allowed to hang for a set time period.

In the third phase, the straightened hair tresses were wetted out with warm tap water at approximately 35-40° C. flowing at about 0.7 gallons/minute [2650 cc/minute] for ten seconds. Then about 2 cc of a commercial shampoo was applied and distributed onto the tresses from top to bottom rubbing the product down and up three times on each side (front/back) with about a 1 minute contact time. The tresses were placed in the palm on one hand and then rinsed for about 30 seconds. Similarly, about 2 cc of a commercial conditioner was applied onto the tresses from top to bottom and distributed by rubbing the conditioner down and up three times on each side (front/back) with about a 1 minute contact time. The tresses were rinsed again for about 30 seconds under warm tap water and then excess water was squeezed out. The tresses were then combed through once with large teeth and then once with small teeth of a two-sided comb. The tresses were then hung to air-dry.

The method using the poly(vinylamine-vinylformamide) copolymer composition with a conditioning agent and the citrate composition with a conditioning agent resulted in improved hair styling with hair that felt natural and was easy to comb, straighten, and wash.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of styling mammalian hair, wherein said method comprises:
    either first contacting the hair for about 1 to 20 minutes with a styling-effective amount of a composition comprising a poly(vinylamine-vinylformamide) copolymer and an aqueous carrier; and
    thereafter contacting the hair for about 1 to 20 minutes with a styling-effective amount of a composition comprising a citrate and an aqueous carrier; or contacting the hair for about 1 to 20 minutes with a styling-effective amount of a composition comprising a citrate and an aqueous carrier; and
    thereafter contacting the hair for about 1 to 20 minutes with a styling-effective amount of composition comprising a poly(vinylamine-vinylformamide) copolymer and an aqueous carrier; and
    subsequently styling the hair by contacting the hair with a device comprising at least one flat surface at a temperature of at least about 100° C. for at least about 1 second to at least semi-permanently, straighten the hair wherein the poly(vinylamine-vinylformamide) copolymer comprises a high molecular weight poly(vinylamine-vinylformamide) copolymer, a low molecular weight poly(vinylamine-vinylformamide) copolymer, or a combination thereof and wherein the citrate is selected from the group consisting of citrate salts of sodium, citrate salts of potassium and citrate salts of calcium.

2. The method of claim 1, wherein the citrate salt of sodium is disodium citrate.

3. The method of claim 1, wherein the high molecular weight poly(vinylamine-vinylformamide) copolymer comprises at most about 95 mol % vinylamine monomers.

4. The method of claim 1, wherein the high molecular weight poly(vinylamine-vinylformamide) copolymer comprises at most about 50 mol % vinyl amine monomers.

5. The method of claim 1, wherein the high molecular weight poly(vinylamine-vinylformamide) copolymer comprises at most about 30 mol % vinyl amine monomers.

6. The method of claim 1, wherein the high molecular weight poly(vinylamine-vinylformamide) copolymer comprises at most about 10 mol % vinyl amine monomers.

7. The method of claim 1, wherein the low molecular weight poly(vinylamine-vinylformamide) copolymer comprises about 95 mol % vinyl amine monomers.

8. The method of claim 1, wherein either composition further comprises a conditioning agent.

9. The method of claim 8, wherein the conditioning agent is present in an amount of about 0.25 wt % to about 1.5 wt %.

10. The method of claim 1, wherein either composition further comprises a surfactant.

11. The method of claim 1, wherein either composition further comprises propellant.

12. The method of claim 11, wherein either composition is in the form of a mousse or a gel.

13. The method of claim further comprising the step of rinsing the hair with water after contacting the hair with both compositions.

* * * * *